(12) United States Patent
Kwon

(10) Patent No.: US 10,467,930 B2
(45) Date of Patent: Nov. 5, 2019

(54) IMAGE-REPLACEABLE FUNCTIONAL ADVERTISEMENT APPARATUS

(71) Applicant: COCOON DESIGN Co., Ltd., Gwangmyeong-si, Gyeonggi-do (KR)

(72) Inventor: Young Jun Kwon, Seoul (KR)

(73) Assignee: COCOON DESIGN Co., Ltd., Gwangmyeong-si (KR)

( * ) Notice: Subject to any disclaimer, the term of this patent is extended or adjusted under 35 U.S.C. 154(b) by 0 days.

(21) Appl. No.: 16/201,567

(22) Filed: Nov. 27, 2018

(65) Prior Publication Data

US 2019/0096293 A1 Mar. 28, 2019

Related U.S. Application Data

(63) Continuation of application No. PCT/KR2017/009618, filed on Sep. 1, 2017.

(30) Foreign Application Priority Data

Jul. 14, 2017 (KR) .......................... 10-2017-0089869

(51) Int. Cl.
*G09F 13/04* (2006.01)
*F21V 23/04* (2006.01)
(Continued)

(52) U.S. Cl.
CPC ............ *G09F 13/0413* (2013.01); *A61L 9/12* (2013.01); *F21V 9/40* (2018.02); *F21V 23/0485* (2013.01);
(Continued)

(58) Field of Classification Search
CPC ... A61L 9/04; A61L 9/048; A61L 9/00; A61L 9/12; G09F 13/00–46; G09F 13/0413;
(Continued)

(56) References Cited

U.S. PATENT DOCUMENTS

| 1,547,160 A * | 7/1925 | Bailey ................. H05B 3/0033 119/73 |
| 3,587,185 A * | 6/1971 | Deal ....................... G09F 13/12 362/293 |

(Continued)

FOREIGN PATENT DOCUMENTS

| JP | 2005-215663 A | 8/2005 |
| KR | 20-1999-0017483 A | 5/1999 |

(Continued)

OTHER PUBLICATIONS

Office Action corresponding to Korean Patent Application No. 10-2017-0089869; mailed by the Korean Intellectual Property Office dated Oct. 24, 2017.

*Primary Examiner* — Cassandra Davis
(74) *Attorney, Agent, or Firm* — Studebaker & Brackett PC

(57) ABSTRACT

Disclosed is an image-replaceable functional advertisement apparatus that includes a base having a plate shape, a shade formed of a flexible material and coupled to a top of the base along a periphery of the base, the shade including an image mounting surface to which an image is attached, a lighting column mounted in an upright position on a side of an upper surface of the base surrounded by the shade, and a cover that covers an open top of the shade.

13 Claims, 11 Drawing Sheets

(51) Int. Cl.
  *F21V 9/40* (2018.01)
  *A61L 9/12* (2006.01)
  *G09F 19/00* (2006.01)
  *F21Y 115/10* (2016.01)
  *G09F 13/22* (2006.01)

(52) U.S. Cl.
  CPC ............ *G09F 13/04* (2013.01); *G09F 19/00* (2013.01); *A61L 2209/12* (2013.01); *A61L 2209/133* (2013.01); *A61L 2209/15* (2013.01); *F21Y 2115/10* (2016.08); *G09F 2013/0445* (2013.01); *G09F 2013/0463* (2013.01); *G09F 2013/0481* (2013.01); *G09F 2013/222* (2013.01)

(58) Field of Classification Search
  CPC ............ G09F 19/00; G09F 2013/0481; G09F 2013/0445; F21V 9/40; F21V 23/0485; F21Y 2115/10
  See application file for complete search history.

(56) References Cited

U.S. PATENT DOCUMENTS

| | | | |
|---|---|---|---|
| 4,346,059 A * | 8/1982 | Spector | A61L 9/03 239/34 |
| 5,309,338 A * | 5/1994 | Liu | A61L 9/122 362/253 |
| 5,651,942 A * | 7/1997 | Christensen | A61L 9/03 422/125 |
| 6,135,622 A * | 10/2000 | Downing | F21S 6/005 362/410 |
| 7,204,618 B1 * | 4/2007 | Kuelbs | F21S 9/037 362/35 |
| 7,314,293 B2 * | 1/2008 | Steier | F21S 6/00 362/351 |
| 8,158,066 B2 * | 4/2012 | Yang | A61L 9/122 40/406 |
| 8,960,975 B2 * | 2/2015 | Yang | F21S 6/001 362/351 |
| 9,779,640 B2 * | 10/2017 | Ruhaak | G09F 1/065 |
| 2017/0027361 A1 * | 2/2017 | Santiago | A47G 33/0836 |

FOREIGN PATENT DOCUMENTS

| | | |
|---|---|---|
| KR | 10-2003-0084878 A | 11/2003 |
| KR | 10-0843671 B1 | 7/2008 |
| KR | 20-2009-0012941 A | 12/2009 |
| KR | 10-2014-0105287 B1 | 9/2014 |

* cited by examiner

IMAGE-REPLACEABLE FUNCTIONAL ADVERTISEMENT APPARATUS

CROSS-REFERENCE TO RELATED APPLICATIONS

The present application is a continuation of International Patent Application No. PCT/KR2017/009618, filed on Sep. 1, 2017, which is based upon and claims the benefit of priority to Korean Patent Application No. 10-2017-0089869, filed on Jul. 14, 2017. The disclosures of the above-listed applications are hereby incorporated by reference herein in their entirety.

BACKGROUND

Embodiments of the inventive concept described herein relate to an image-replaceable functional advertisement apparatus, and more particularly, relate to an image-replaceable functional advertisement apparatus that includes a shade for surrounding a lighting device located in the center thereof, and a base and a cover for fixing the shade and the lighting device, enabling the shade to be freely replaced and thereby creating various advertisements or lighting effects.

In general, the term "point of purchase (POP) advertisement" refers to all advertisements installed in the front of, within, and around a retail store. POP advertisement, including outdoor signage, a poster, and a panel of a retail store and a display of a store, is very widely used as a modern advertisement medium.

A considerable number of prefabricated POP advertisement apparatuses for ease of installation and simplicity of storage are disclosed in the related art. The prefabricated POP advertisement apparatuses provide structures for easily attaching/detaching or assembling advertising panels having advertisement images printed thereon and include lighting devices in order to provide high visibility of the advertisement images even in the dark.

However, the advertisement apparatuses with the lighting devices have complex structures due to the lighting devices and therefore fail to provide ease of installation and operation. Furthermore, in the case where advertisements are manufactured in three dimensions to double advertisement effects, the structures of the advertisement apparatuses may be unnecessarily complex, which may lead to an increase in manufacturing cost and degradation in utilization.

In addition, the advertisement apparatuses simply occupy spaces in daylight when the lighting devices are turned off or while the advertisement apparatuses are not used. Therefore, unless other components for diversely utilizing the advertisement apparatuses are added, the advertisement apparatuses have no additional benefit for users, except that rapid replacement is possible, compared to conventional advertising panels.

Accordingly, it is required to develop a novel and advanced advertisement apparatus that can enhance ease of assembly and installation despite a lighting device, can be semi-permanently used due to ease of replacement of an advertisement image, and can be naturally used in real life through additional functions even when not serving as an advertisement.

The following prior arts have been proposed to overcome these problems.

The "prefabricated plastic POP display stand with a robust structure" disclosed in Korean Patent No. 10-0843671 includes a plurality of display plates 210 molded under vacuum and a plurality of connecting rods 250 vertically connecting the plurality of display plates 210 to form multiple stages. Each of the display plates 210 includes a tray 211 on which goods are placed, connection recesses 213 for arranging the display plates 210 in multiple stages, and protrusions 214 corresponding to the connection recesses 213, in which the connection recesses 213 and the protrusions 214 are formed on the corners of the display plate 210. The tray 211 has a reinforcing groove 212 formed thereon under vacuum, and the reinforcing groove 212 is open at the top thereof and further protrudes downward beyond the other portion. A first reinforcing member 220 is fixedly inserted into the reinforcing groove 212 to reinforce the tray 211. In addition, the POP display stand further includes a second reinforcing member 230 inserted into each connection recess 213 to reinforce the connection recess 213, a third reinforcing member 240 mounted on each protrusion 214 to reinforce the protrusion 214, and a pair of supports 217 integrally formed with the rear surface of the display plate 210 to support an advertising panel 260. The above-configured POP display stand can achieve a robust structure, as well as low cost and sufficient strength.

However, the POP display stand may be difficult to use in the dark since the POP display stand does not include a separate lighting device.

The "foldable banner of a stand type" disclosed in Korean Patent Publication No. 10-2003-0084878 includes: a banner 30 including a banner base 31 formed of a flexible material, an advertisement surface 32 that is located on the central portion of the banner base 31 and on which advertisement contents are printed, and connectors 34 and 35 formed at opposite sides of the advertisement surface 32 in multiple stages with fold lines 33 at opposite ends of the advertisement surface 32, the connectors 34 and 35 being folded toward the back side of the advertisement surface 32 and connected together; insertion protrusions 36 and insertion slots 37 for coupling the connectors 34 and 35; and insertion portions 39 that are formed in the connectors 34 and 35 and to which elastic means 38 are connected to consistently maintain the shape of the advertisement surface 32. The above-configured foldable banner is advantageous in that the completed banner can be easily stored and delivered and can be easily installed and stored on a site.

Although the advertisement surface is easy to replace, the banner may be difficult to use in the dark since the banner does not include a separate lighting device for illuminating the advertisement surface.

SUMMARY

Embodiments of the inventive concept provide an advertisement apparatus that is built by assembling a base, a lighting column, a shade, and a cover that are made in standard sizes.

Embodiments of the inventive concept provide an advertisement apparatus that enables a shade to be easily replaced.

Embodiments of the inventive concept provide an advertisement apparatus having a flavoring function using a flavoring agent mounted therein.

Embodiments of the inventive concept provide a grip that enables the scent of a flavoring agent to easily spread to the outside without affecting the external appearance of a shade.

According to an aspect of an embodiment, an image-replaceable functional advertisement apparatus includes a base having a plate shape, a shade formed of a flexible material and coupled to a top of the base along a periphery of the base, the shade including an image mounting surface to which an image is attached, a lighting column mounted in an upright position on a side of an upper surface of the base surrounded by the shade, and a cover that covers an open top of the shade.

The shade may further include an opening cut along a height direction of the shade and extensions extending inward from opposite ends of the opening. The base may include a fixing recess into which lower portions of the extensions are fixedly inserted, and the fixing recess may be concavely formed at a location corresponding to the extensions.

The lighting column may include a support that protrudes along a periphery of the lighting column and supports the cover.

The lighting column may be mounted through the cover such that an end portion of the lighting column is exposed to the outside. The lighting column may further include a touch switch on the exposed end portion, and the touch switch may recognize a touch signal and may perform on/off control of an LED.

The image-replaceable functional advertisement apparatus according to the inventive concept provides the following advantageous effects:

(1) The advertisement apparatus can be completed by simple insertion assembly.

(2) A user can replace the shade to display various advertisements or images.

(3) The advertisement apparatus can release the scent of a flavoring agent mounted therein to the outside.

(4) The grip enables the scent of a flavoring agent to easily spread to the outside and can fix the form of the shade without affecting the external appearance of the shade.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Figure 1:
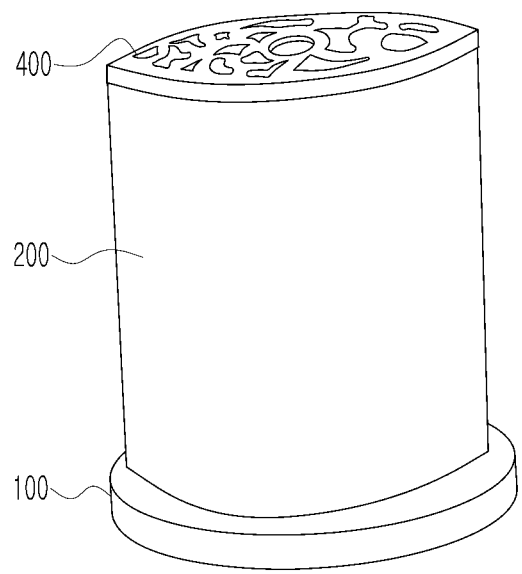
FIG. 1 is a view illustrating a basic configuration of an advertisement apparatus according to the inventive concept.

An image-replaceable functional advertisement apparatus according to the inventive concept may include a base having a plate shape, a shade formed of a flexible material and coupled to a top of the base along a periphery of the base, the shade including an image mounting surface to which an image is attached, a lighting column mounted in an upright position on a side of an upper surface of the base surrounded by the shade, and a cover that covers an open top of the shade.

Hereinafter, exemplary embodiments of the inventive concept will be described in detail with reference to the accompanying drawings. The drawings are not shown according to scale, and the same reference numerals are used throughout the different drawings to designate the same or similar components.

Figure 2A:
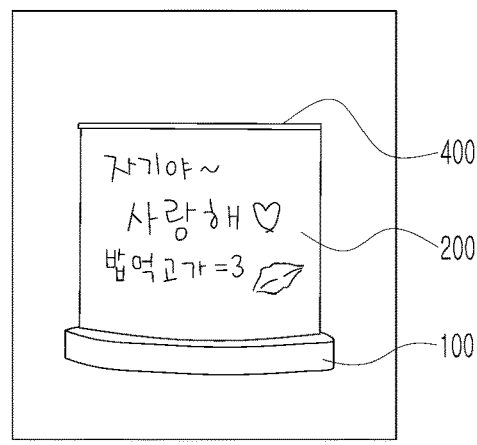
FIGS. 2A and 2B are views illustrating examples of the advertisement apparatus according to the inventive concept.
Figure 2B:
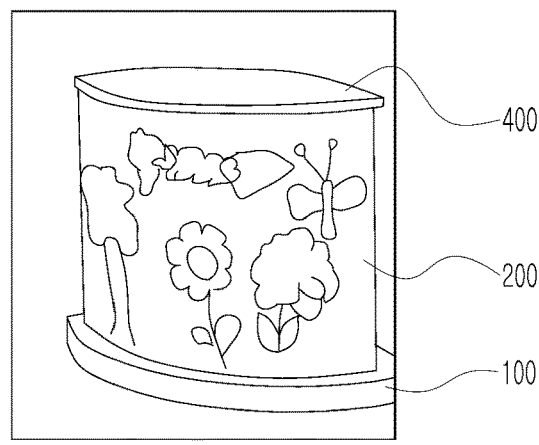
Figure 3A:
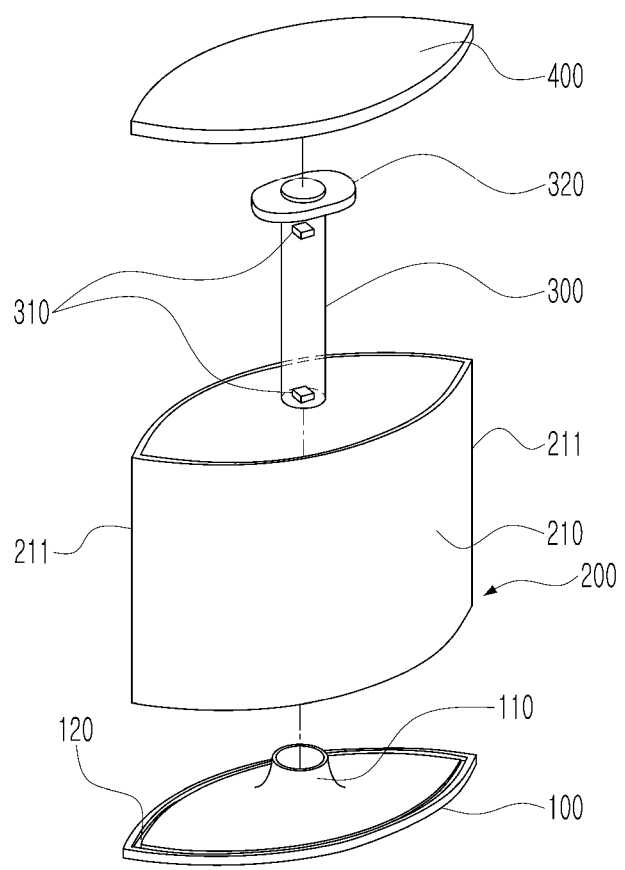
FIGS. 3A and 3B are views illustrating a basic configuration of the advertisement apparatus according to the inventive concept.
Figure 3B:
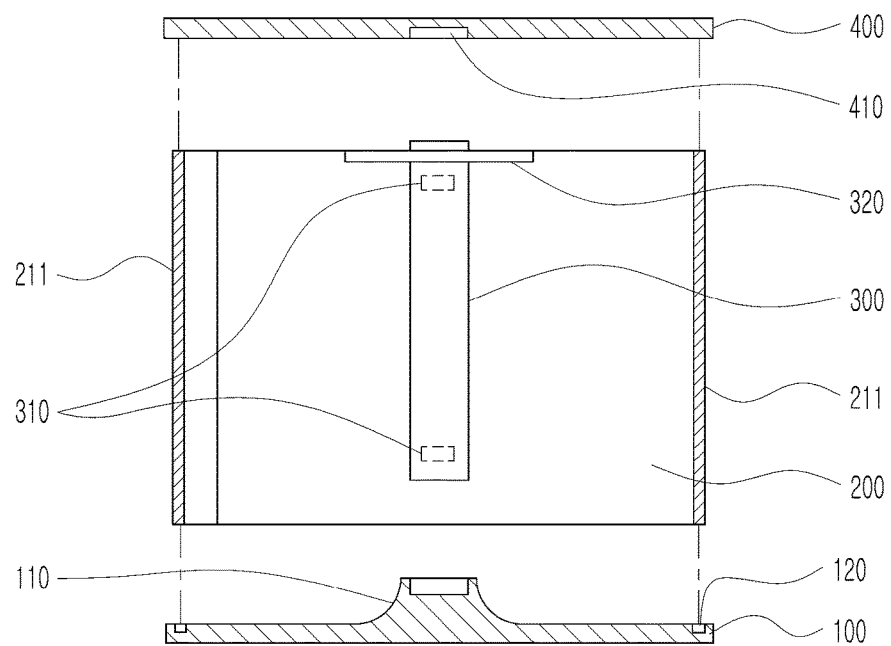
Figure 4A:
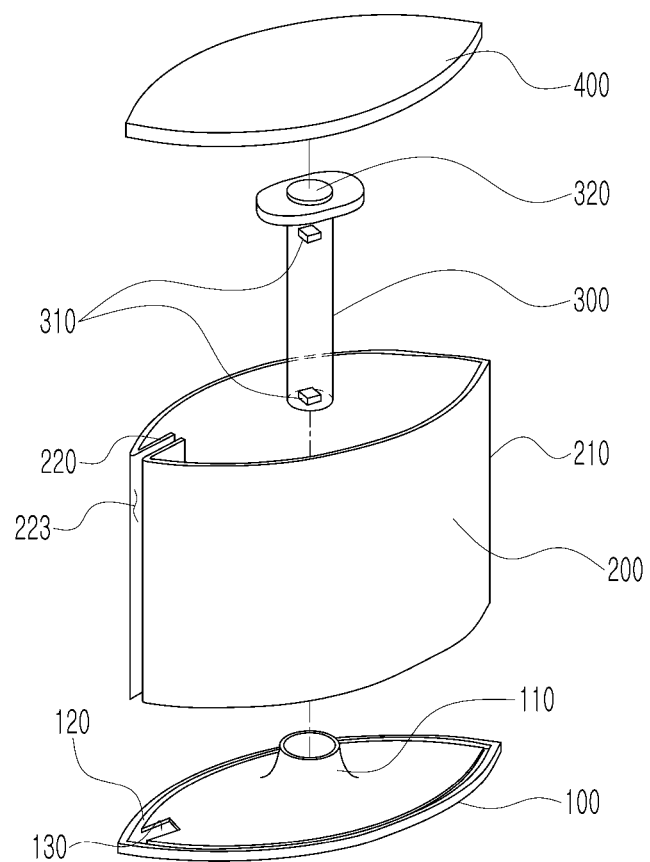
FIGS. 4A and 4B are views illustrating an extended configuration of the advertisement apparatus according to the inventive concept.
Figure 4B:
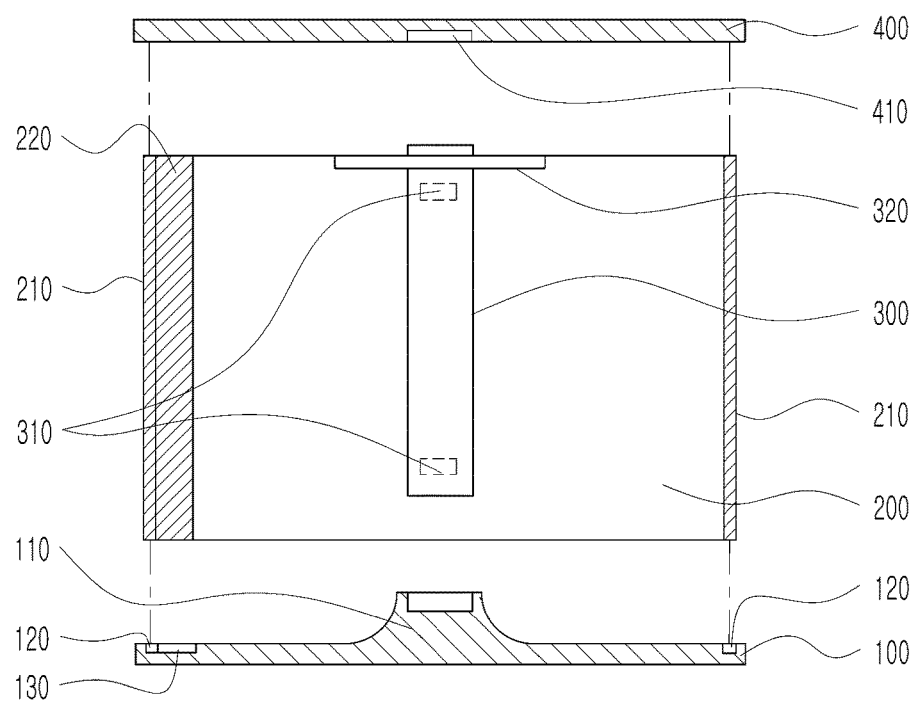

FIG. 1 is a view illustrating a basic configuration of an advertisement apparatus according to the inventive concept. FIGS. 2A and 2B are views illustrating examples of the advertisement apparatus according to the inventive concept. FIGS. 3A and 3B are views illustrating a basic configuration of the advertisement apparatus according to the inventive concept. FIGS. 4A and 4B are views illustrating an extended configuration of the advertisement apparatus according to the inventive concept.

The advertisement apparatus according to the inventive concept may include a base 100 having a plate shape, a shade 200 formed of a flexible material and coupled to a top of the base 100 along a periphery of the base 100, the shade 200 including an image mounting surface 210 to which an image is attached, a lighting column 300 mounted in an upright position on a side of an upper surface of the base 100 surrounded by the shade 200, and a cover 400 that covers an open top of the shade 200.

As can be seen in FIG. 1, the shade 200 may be formed of a flexible (elastic) material, for example, coated/chemically-treated paper or fabric, a synthetic resin, or the like. The shade 20 may include the image mounting surface 210 to which an image of a desired size is attached. The area of the shade 200 may be varied with the size of an image to be attached. The image may be attached to, or printed or directly drawn on, the image mounting surface 210.

The image mounting surface 210 of the shade 200, as illustrated in FIGS. 2A and 2B, may be used for various purposes.

The shade 200, as illustrated in FIGS. 3A to 4B, may further include two folding portions 211 that extend from top to bottom along the lengthwise direction of the shade 200. The folding portions 211 enable the shade 200 to be folded and stored in the flat state or to be unfolded and transformed into a three-dimensional structure. To this end, the shade 200 may basically include one folding portion 211 that vertically passes through the center of the shade 200, and the other folding portion 211 may be additionally included in the shade 200. Accordingly, the shade 200 may be transformed into various three-dimensional structures.

For example, in order to transform a piece of paper into a cylindrical shape with an elliptic cross-section, the folding portion 211 may be formed to pass through the center of the paper, and when the paper needs to be stored, the folding portion 211 enables the paper to be folded and stored in a rectangular form. Therefore, the one folding portion 211 may be basically formed, and more folding portions 211 may be formed to transform the paper into a complex form Referring to FIGS. 3A to 4B, the shade 200 may be shaped in a roll form and may have a space formed therein. The lighting column 300 extending along the lengthwise direction may be located in the space. The lighting column 300 may include a column and LEDs 310 therein (or a light such as an incandescent lamp or a fluorescent lamp). The column has to be formed of a light transmissive material (a transparent or translucent material) to sufficiently transfer light emitted from the LEDs 310 to the outside.

In addition, members are required to cover the open top and bottom of the shade 200 in the state in which the shade 200 and the lighting column 300 are provided as described above. To this end, the advertisement apparatus may further include the base 100 at the bottom of the shade 200 and the cover 400 at the top of the shade 200.

The base 100 may have a light mounting portion 110 to which a lower end portion of the lighting column 300 is coupled. The light mounting portion 110 may be located at the center of the base 100. The light mounting portion 110 enables the lighting column 300 to be fixed in an upright position, with the lower end portion of the lighting column 300 coupled to the light mounting portion 110. In addition, a power line or a control line may be connected to the lighting column 300 via the light mounting portion 110 to receive electric power from the outside and transfer the electric power to the lighting column 300. The light mounting portion 110 may be recessed simply into the base 100 similarly to a socket, or may be formed through the base 100.

Even if the light mounting portion 110 is excluded, the base 100 may selectively include a mounting guide 120 into which part of the bottom of the shade 200 is fixedly inserted. The mounting guide 120 may be spaced apart from the light mounting portion 110 and may be recessed along the periphery of the base 100 (or at predetermined intervals). Although the shade 200 may be mounted on the base 100 along the periphery of the base 100, the mounting guide 120 may be used as a groove into which the shade 200 is inserted. The entire bottom of the shade 200 does not have to be fixedly inserted into the mounting guide 120. Therefore, the mounting guide 120 may be formed every predetermined interval, or only one mounting guide 120 may be formed when it is determined that the mounting guide 120 can sufficiently support the shade 200.

The advertisement apparatus may further include the cover 400 for covering the open top of the shade 200 in the state in which both the lighting column 300 and the shade 200 are fixed to the base 100. The cover 400 may have a light coupling portion 410 formed thereon, to which an upper end portion of the lighting column 300 is coupled. Likewise to the light mounting portion 110, the light coupling portion 410 may be formed at the center of the cover 400. Even in this case, the light coupling portion 410 may be recessed simply into the cover 400 similarly to a socket, or may be formed through the cover 400.

The cover 400 and the base 100 may have top and bottom shapes that correspond to a form to be implemented in three dimensions by the shade 200. For example, when the base 100 and the cover 400 have a square shape, the shade 200 fixed via the mounting guide 120 of the base 100 may also be fixed in the same square form to finally have a hexahedron shape. In another example, when the base 100 and the cover 400 have an elliptic shape, the shade 200 may finally have an elliptic cylindrical shape. By applying this configuration, a sculpture in a complex form may be placed on the cover 400 and may be used like a statue.

As illustrated in FIGS. 4A and 4B, the shade 200 may be formed to surround the periphery of the base 100, with one side of the shade 200 open. The shade 200 may further include extensions 220 extending inward from opposite ends of the open side thereof. In other words, an opening 223 may be formed along the height direction of the shade 200, and the extensions 220 may extend inward from opposite ends of the opening 223. Correspondingly, the base 100 may further include a fixing recess 130 into which lower portions of the extensions 220 are fixedly inserted. The fixing recess 130 may be formed on the surface of the base 100 to correspond to the extensions 220, or may extend from one side of the mounting guide 120 toward the inside of the base 100.

The extensions 220 and the fixing recess 130 may assist in fixing the shade 200. That is, the extensions 220 may be folded at the distal ends of the shade 200 and may prevent the shade 200 from falling. In addition, the lower portions of the extensions 220 may be additionally inserted into the fixing recess 130 to fix the form of the shade 200.

The lighting column 300 may further include a support 320 for supporting the cover 400. The support 320 may be mounted on a side of the outer circumferential surface of the lighting column 300. The support 320 may be formed on the border between the lighting column 300 and the cover 400 when the lighting column 300 is inserted into the light coupling portion 410 of the cover 400. The support 320 may extend parallel to the cover 400 and may have a predetermined area. The support 320 is intended to solve the problem that, when only the light coupling portion 410 is formed on the cover 400, the cover 400 rotates so that the lighting column 300 is separated from the cover 400. In addition to the coupling of the lighting column 300 and the light coupling portion 410, the support 320 may additionally support the cover 400, so that the lighting column 300 and the cover 400 may be easily coupled together and the coupling force may be increased, compared with the existing configuration. The cover 400 may have, on the bottom thereof, a recess corresponding to the shape of the support 320 to specify a region where the support 320 is located (preferably, inserted). In some cases, the light coupling portion 410 may be formed through the cover 400, instead of being recessed into the bottom thereof. Alternatively, magnetic coupling may be formed between the support 320 and the cover 400 such that the support 320 and the cover 400 are coupled together by magnetic attraction force therebetween.

Figure 6:
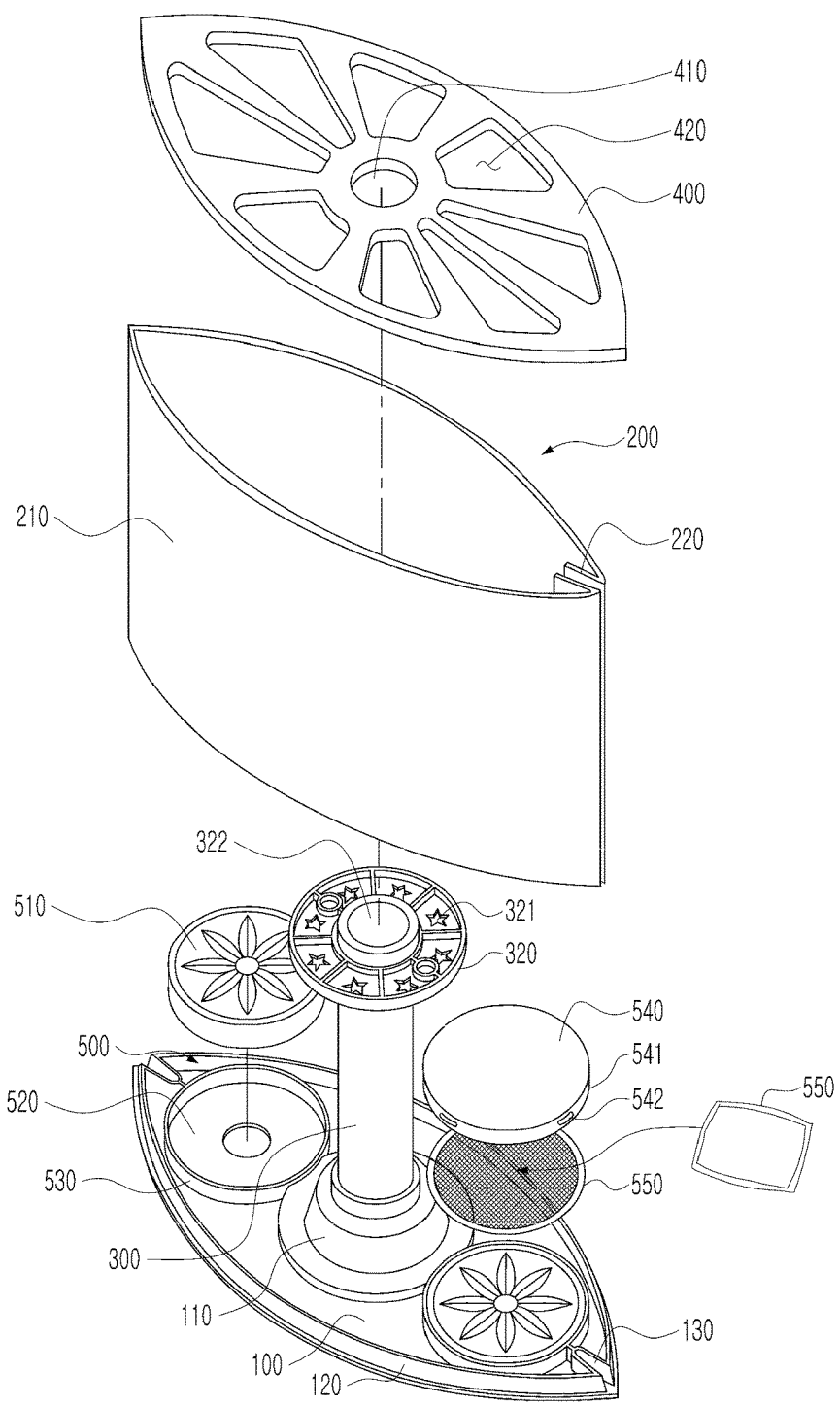
FIG. 6 is an exploded perspective view illustrating an extended configuration in which the flavoring agent is applied to the advertisement apparatus according to the inventive concept.

Referring to FIG. 6, in the case where the light coupling portion 410 is formed through the cover 400, the lighting column 300 may further include a touch switch 322 on an end portion that is inserted into the light coupling portion 410. That is, the touch switch 322 may be exposed outside the cover 400 via the light coupling portion 410, and therefore a user may touch the exposed touch switch 322 to operate the lighting column 300. The touch switch 322 may be operable in conjunction with the LEDs 310 to perform on/off control of the LEDs 310. For example, the LEDs 310 may emit light bulb color (orange-colored) light when the touch switch 322 is touched once, white light when the touch switch 322 is touched twice, and a mixture thereof when the touch switch 322 is touched three times, and may be turned off when the touch switch 322 is touched four times. In addition, the LEDs 310 may be turned off when a touch signal is input for a specified period of time or longer.

As described in section "BACKGROUND", the advertisement apparatus according to the inventive concept may have problems in that, while the LEDs 310 are turned off, persons around the advertisement apparatus can perceive advertisements only when the ambient light is sufficient, and the advertisement apparatus simply occupies space after being used in advertisement. In order to solve the above-mentioned problems, the advertisement apparatus may further include the following components.

Figure 5:
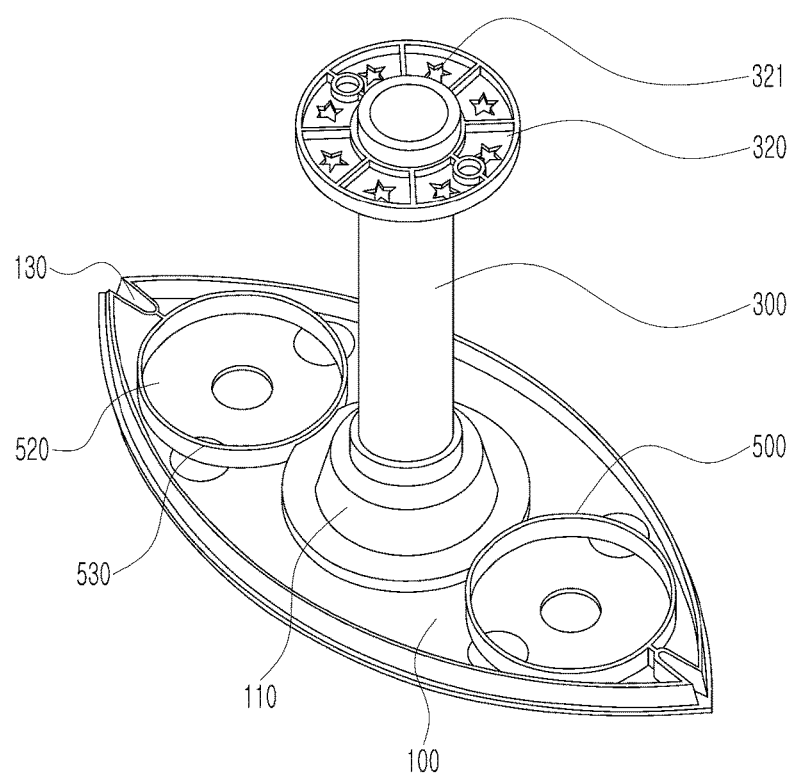
FIG. 5 is a perspective view illustrating an internal configuration in which a flavoring agent is applied to the advertisement apparatus according to the inventive concept.

FIG. 5 is a perspective view illustrating an internal configuration in which a flavoring agent 510 is applied to the advertisement apparatus according to the inventive concept. FIG. 6 is an exploded perspective view illustrating an extended configuration in which the flavoring agent 510 is applied to the advertisement apparatus according to the inventive concept.

Referring to FIGS. 5 and 6, the base 100 may further include a flavoring agent holder 500 that includes the flavoring agent 510 that releases a scent, a circular holder base 520 seated on the surface of the base 100, and a positioning guide 530 that circularly surrounds the periphery of the holder base 520 to form a storage space for the flavoring agent 510.

The flavoring agent 510 may be formed in a gel or solid form. Alternatively, the flavoring agent 510 may be formed in a powder or liquid form. In this case, the flavoring agent 510 may be coated with a membrane or may be placed in a storage bag or a net. The coating or the storage bag has to have fine holes to release the scent of the flavoring agent 510 to the outside. Since the storage space for the flavoring agent 510, which is formed by the holder base 520 and the positioning guide 530, has a cylindrical shape, the flavoring agent 510 to be stored may preferably have a cylindrical shape to match the storage space.

The holder base 520 may prevent the flavoring agent 510 from directly touching the surface of the base 100. Accordingly, the holder base 520 may prevent the flavoring agent 510 from corroding the base 100, or may prevent the flavoring agent 510 from oxidizing. The positioning guide 530 may extend perpendicular to the holder base 520 along the periphery thereof to form the storage space for the flavoring agent 510. Since the depth (size) of the storage space for the flavoring agent 510 varies with the height of the holder base 520, the height of the holder base 520 has to be determined in careful consideration of the storage capacity.

The cover 400 may additionally have a plurality of flavoring holes 420 formed therethrough, and the scent of the flavoring agent 510 may be released to the outside via the flavoring holes 420. The flavoring holes 420 have no limitation in size or shape, and various structures, such as a specific pattern or a letter-shaped hole, may be applied to the flavoring holes 420. In this case, as illustrated in FIGS. 5 and 6, the support 320 may also have through-holes 321 formed therein to correspond to the flavoring holes 420. Likewise to the flavoring holes 420, the through-holes 321 may have various forms or sizes.

Additionally, it can be seen in FIGS. 5 and 6 that the flavoring agent holder 500 is open at the top thereof. Some users, when inhaling the scent right by the flavoring agent 510, may have a headache due to the too strong scent. Further, if the flavoring agent 510 always releases the scent, the lifespan of the flavoring agent 510 may be somewhat shortened, and therefore the flavoring agent 510 may be frequently replaced. Accordingly, the flavoring agent holder 500 may further include a flavoring agent cover 540 that is coupled to the top of the flavoring agent holder 500 so as to be opened or closed when the user wants to stop using the flavoring agent 510. The flavoring agent cover 540 may have a plate shape that covers the top of the flavoring agent holder 500. In addition, in order to increase a fixing force, the flavoring agent cover 540 may further include a wall that is press fit onto the holder base 520. Alternatively, the flavoring agent cover 540 may be hinged to the flavoring agent holder 500 to prevent separation from the flavoring agent holder 500.

The flavoring agent cover 540 including the wall may be the most basic form of the flavoring agent cover 540 that the inventive concept aims for. Specifically, the flavoring agent cover 540 may include a cover wall 541 extending perpendicular to the flavoring agent cover 540 along the periphery thereof, stoppers 542 protruding from the inner circumferential surface of the cover wall 541, a net 550 supported by the stoppers 542, and a moisture absorbent pad 560 seated on the net 550. That is, the moisture absorbent pad 560 may be placed inside the flavoring agent cover 540 to prevent the flavoring agent 510 from being wet when stored in the flavoring agent holder 500. The moisture absorbent pad 560 may serve to absorb moisture in the air. The moisture absorbent pad 560 may be composed of silica gel. The silica gel may serve to absorb moisture in the air. Since silica gel can be freely processed into various forms, the silica gel may be processed in a desired shape or size and may be used as the moisture absorbent pad 560.

Figure 7A:
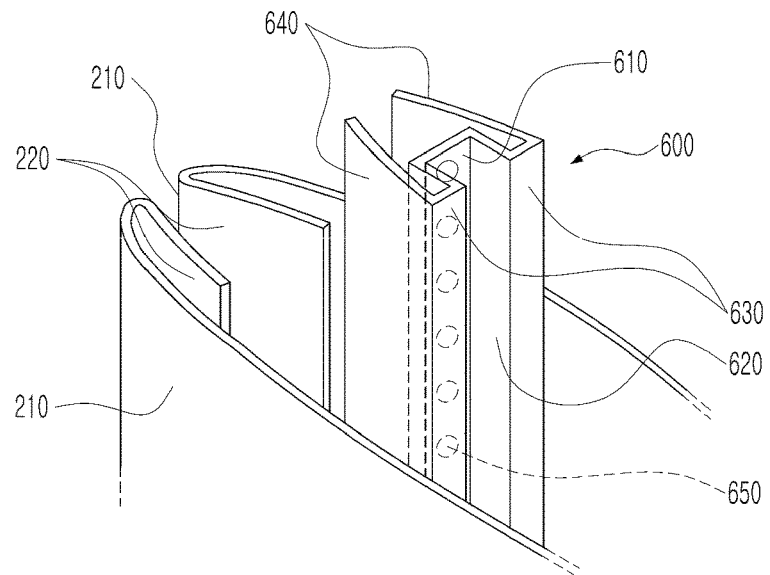
FIGS. 7A and 7B are views illustrating a configuration in which a spacer is applied to the advertisement apparatus according to the inventive concept.
Figure 7B:
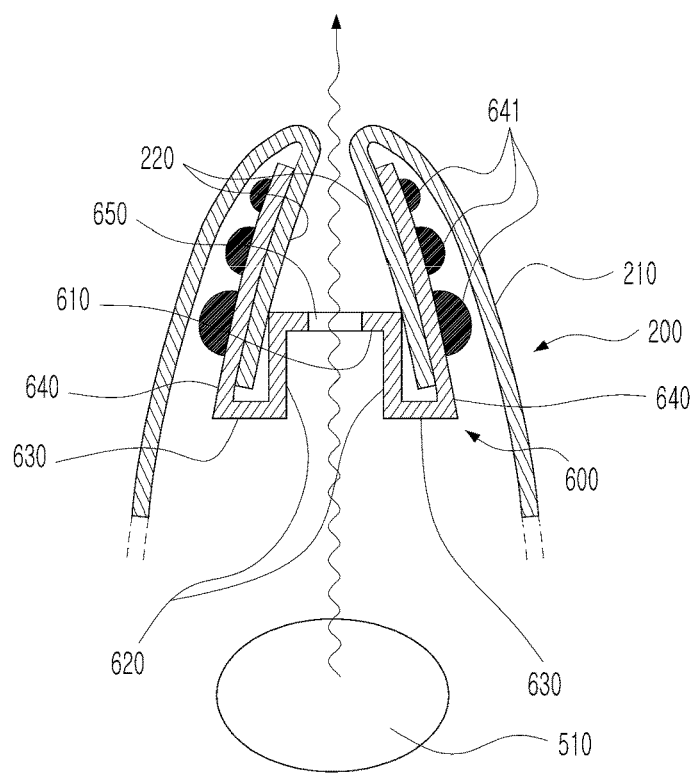

FIGS. 7A and 7B are views illustrating a configuration in which a spacer 600 is applied to the advertisement apparatus according to the inventive concept.

A configuration to use the extensions 220 may be further included in the configuration in which the favoring agent 510 is added to the advertisement apparatus. That is, the advertisement apparatus may further include the spacer 600 that includes auxiliary flavoring surfaces 640 obliquely extending toward the inside of the shade 200 in the spaces between the image mounting surface 210 and the extensions 220 and having a greater length than the extensions 220, auxiliary insertion surfaces 630 extending from inside ends of the auxiliary flavoring surfaces 640 in parallel to a virtual extension line that connects distal ends of the pair of extensions 220, auxiliary extension surfaces 620 perpendicularly extending from inside ends of the auxiliary insertions surfaces 630 toward the space between the extensions 220 and having a smaller length than the auxiliary flavoring surfaces 640, and a flavoring extension surface 610 connecting outside ends of the auxiliary extension surfaces 620 and including a plurality of flavoring holes 650 formed therethrough at predetermined intervals along the height direction of the shade 200.

As can be seen in FIG. 7A, the spacer 600 may be inserted between the two extensions 220 to increase the gap between the extensions 220 and simultaneously fix the distal ends of the extensions 220 with the increased gap therebetween. Outside ends of the auxiliary flavoring surfaces 640 may be located ahead of the flavoring extension surface 610 such that an entrance 231 has a smaller width than the inside when the gap between the extensions 220 is increased by the spacer 600. Accordingly, when viewed from the outside, a slit with a small width may appear to be formed. However, a large groove continuous with the inside of the shade 200 may be actually formed. The plurality of flavoring holes 650 may be formed through the flavoring extension surface 610 at the predetermined intervals along the height direction of the shade 200 to release the scent of the flavoring agent 510 into the space between the extensions 220.

A grip will be described in detail with reference to FIG. 7B. The extensions 220 may be inserted into the spaces surrounded by the auxiliary flavoring surfaces 640, the auxiliary insertion surfaces 630, and the auxiliary extension surfaces 620. As mentioned above, the auxiliary flavoring surfaces 640 may obliquely extend ahead of the flavoring extension surface 610. Accordingly, the extensions 220 may be obliquely supported by the auxiliary flavoring surfaces 640 in the same manner, and thus, when viewed from the outside, the wide inner flavoring extension surface 610 may not be visible well due to the narrow gap between the extensions 220. In this case, the outside ends of the auxiliary flavoring surfaces 640 have to be spaced apart from each other to form the gap between the extensions 220.

However, the borders between the image mounting surface 210 and the extensions 220 may always be pointed due to the form of the spacer 600. In addition, the extensions 220 may be easily torn due to the pointed borders. To solve these problems, the spacer 600 may further include spacing protrusions 641 formed of an elastic material. The spacing protrusions 642 may protrude from the outer sides of the auxiliary flavoring surfaces 640 at predetermined intervals along the lengthwise direction. The heights of the respective spacing protrusions 641 may gradually increase from the inside ends to the outside ends, or vice versa, along the lengthwise direction of the auxiliary flavoring surfaces 640. As a result, the image mounting surface 210 may have a desired shape or angle rather than the pointed shape.

Figure 8:
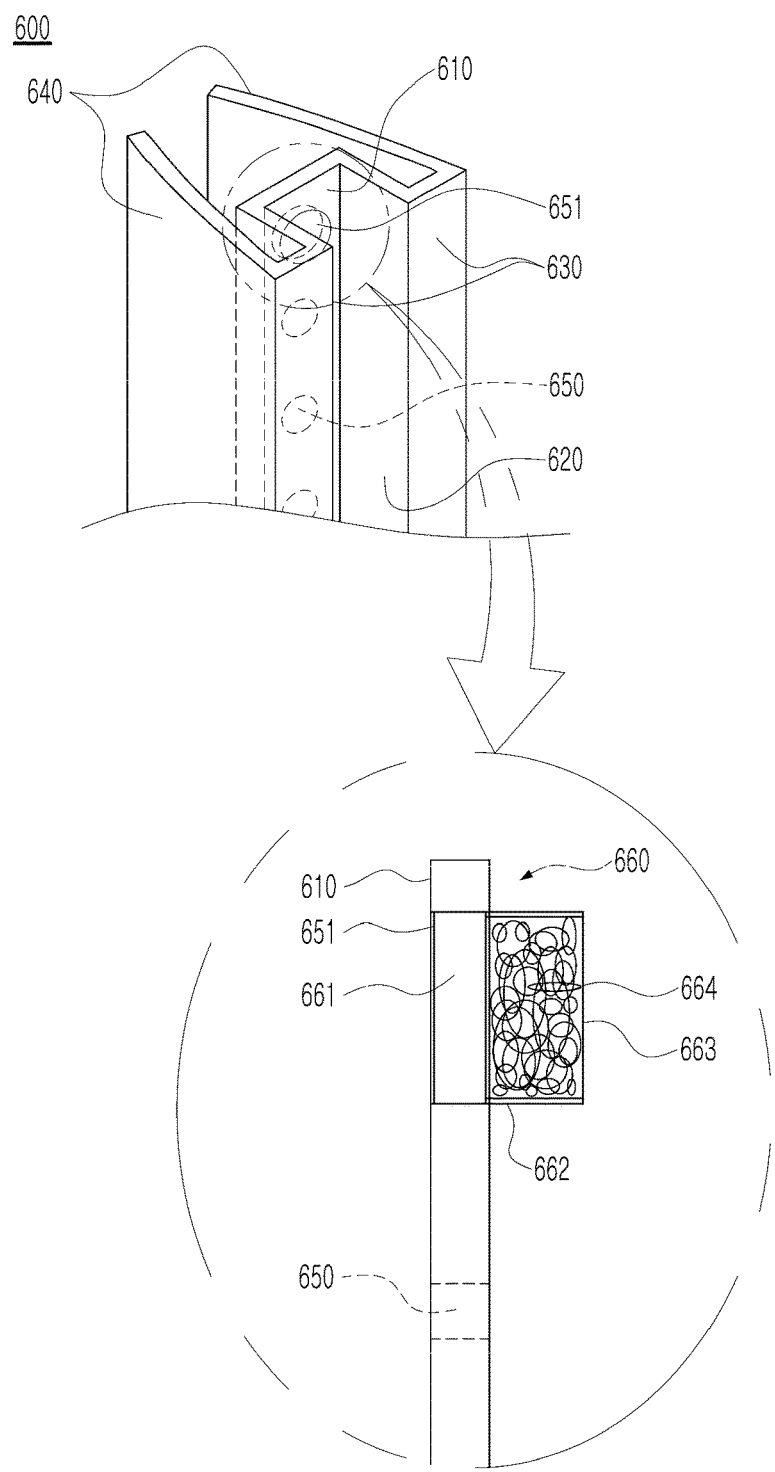
FIG. 8 is a view illustrating the spacer according to the inventive concept.

FIG. 8 is a view illustrating the spacer 600 according to the inventive concept.

When the flavoring agent 510 is used for a predetermined period of time or longer, it may be difficult to rapidly notice the end of the lifespan of the flavoring agent 510 even though the scent of the flavoring agent 510 fills the surrounding air and the lifespan of the flavoring agent 510 ends. In particular, when the flavoring agent 510 in a liquid or solid phase is used, the user may frequently observe the interior of the advertisement apparatus to determine a reduction in the size of the flavoring agent 510. However, when the flavoring agent 510 mixed with gypsum is used, the user has to take out the flavoring agent 510 and inhale the scent thereof in order to determine the end of the lifespan of the flavoring agent 510 because the flavoring agent 510 simply loses the flavoring function without a change in volume or shape.

To solve the above-mentioned problems, the following components may be further included in the advertisement apparatus.

The flavoring agent 510 may contain any one selected from methoxybenzoic acid and sodium benzoate as an effective gradient. The methoxybenzoic acid or the sodium benzoate may have a chemical characteristic that it can increase the lifespan of the flavoring agent 510, compared to alcohol or water with which flavoring gradients are mixed. The methoxybenzoic acid or the sodium benzoate may be used as an ingredient of the flavoring agent 510 at a rate of about 5% to about 20%. Since the methoxybenzoic acid or the sodium benzoate is a benzoic acid-based substance, the methoxybenzoic acid or the sodium benzoate may be characterized in that it has an acidity of pH 5 to pH 7 in itself. If this substance is contained in the flavoring agent 510, the substance may be gasified together when the flavoring gradients are released. Therefore, when the flavoring agent 510 is in operation, the lifespan of the flavoring agent 510 may be noticed by determining whether the acidic ingredient is contained in the flavoring gradients.

In order to detect the acidic ingredient, any one of the flavoring holes 650 of the spacer 600 may be formed to be a sub-hole 651 that has a larger area than the other flavoring holes 650, and the advertisement apparatus may further include a flavoring-agent replacement guide apparatus 660 that includes a stationary part 661 formed of a transparent material and fixedly inserted into the sub-hole 651, a stationary wall 662 extending toward the inside of the shade 200 along the periphery of the stationary part 661 and forming a mounting space with the stationary part 661, an opening 663 formed at one side of the stationary wall 662 that is opposite the stationary part 661, and an indicator 664 embedded in the mounting space, the indicator 664 being a mixture of any one indicating agent selected from metanil yellow, methyl orange, methyl red, cresolphthalein, thymolphthalein, bromothymol blue, and alizarine yellow R and any one adhesive selected from an acrylic adhesive and a silicone adhesive.

The stationary part 661 may clog the sub-hole 651 to prevent air or foreign matter from being introduced into the indicator 664 from the outside. The mounting space may be formed by the stationary wall 662 that extends along the periphery of the stationary part 661. A mixture of an indicating agent such as metanil yellow or methyl orange, which reacts with an acidic material to change its color, and any one of an acrylic adhesive and a silicone adhesive may be embedded in a solid or gel state in the mounting space. The adhesive may not only reduce the restoration time of the indicating agent during which the indicating agent reacts with an acidic material to change its color and returns to the original color after the acidic material disappears, but may also fix the indicating material to prevent the indicating material from being separated from the mounting space. The color change of the indicating material may be visible to the naked eyes through the space between the extensions 220, and when the spacer 600 and the extensions 220 are formed of a light transmissive material, the color of the indicating material may be more easily visible from the outside.

Figure 9:
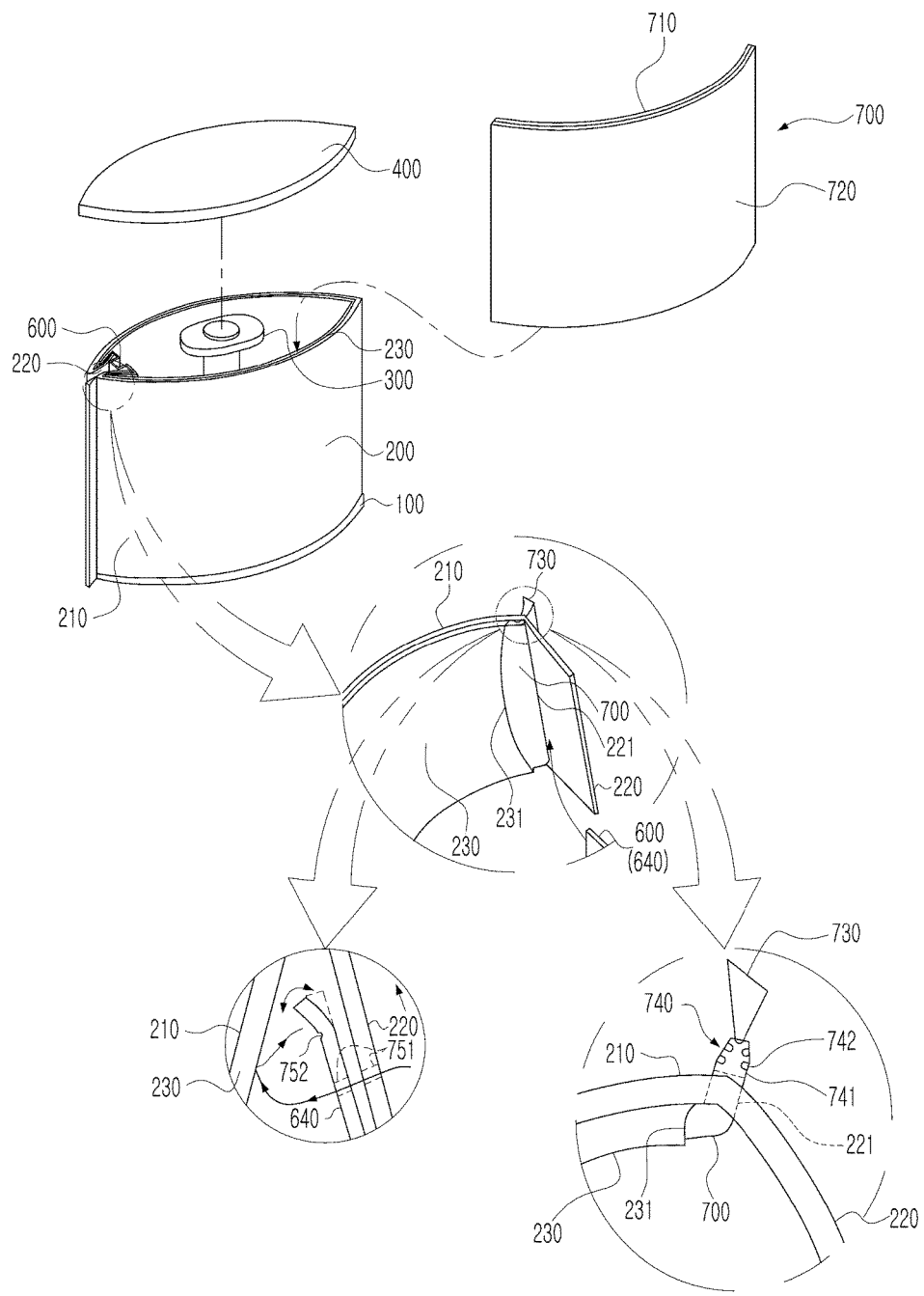
FIG. 9 is a view illustrating a configuration in which a filter sheet is applied to the advertisement apparatus according to the inventive concept.

FIG. 9 is a view illustrating a configuration in which a filter sheet 700 is applied to the advertisement apparatus according to the inventive concept.

Another configuration to use the shade 200 may be additionally applied, in addition to the configuration to use the flavoring agent 510. The advertisement apparatus may further include filter pockets 230 formed on the back side of the image mounting surface 210 and filter sheets 700 inserted into the filter pockets 230. The filter pockets 230 may be formed of a light transmissive material and may have the entrance 231 formed at one side thereof and a storage space formed therein. The filter sheets 700 may lower the illuminance of light transmitting therethrough and may provide the light to the image mounting surface 210.

The filter pockets 230 may be, for example, pockets formed of a transparent material such as vinyl, and the filter sheets 700 may be embedded in the filter pockets 230 to firstly modulate light emitted from the lighting column 300 and irradiate the modulated light to the image mounting surface 210. Both the filter pockets 230 and the filter sheets 700 need not have the same area as the image mounting surface 210. The filter pockets 230 and the filter sheets 700 may be configured such that this light effect is applied to only part of an image mounted on the image mounting surface 210.

The filter sheets 700 may also be formed of a light transmissive material. Each of the filter sheets 700 may include a photochromic layer 710 coated with thermochromic pigment, the transparency of which varies according to a temperature change, and a sensitive layer 720 laminated on the photochromic layer 710 and coated with thermally sensitive pigment having a temperature change section different from the temperature change section of the photochromic layer 710.

The thermochromic pigment may be basically provided in various colors. Thermochromic ink may refer to an ink that develops color in a specific temperature range. The thermochromic ink may have a characteristic that it develops color or is decolorized due to a compound structure change when absorbing heat and returns to the original compound structure when heat is blocked. Accordingly, any ink capable of developing color or being decolorized by heat may be used without limitation. For example, the thermochromic ink may develop color or be decolorized when temperature is raised by heat accumulated as the lighting column 300 emits light. Therefore, the thermochromic ink may allow a corresponding portion to have a specific color or appear to be more transparent when temperature rises.

The thermally sensitive pigment may have the same characteristic as the thermochromic pigment, but may differ from the thermochromic pigment in terms of the temperature change section in which color development or decolorization takes place. The temperature change section may be controlled by adjusting the content of thermochromic ink. For example, when 5 to 15 parts by weight of thermochromic ink is mixed with another ink or a solvent, the thermally sensitive pigment may be discolored at 25 to 30 degrees Celsius. The thermally sensitive pigment may be discolored at a higher temperature with a decrease in the content of the thermochromic ink. Therefore, light transmittance may be controlled by adjusting the content of the thermochromic ink.

In addition, the spacer 600 and the extensions 220 may be formed of a light transmissive material. The entrances 231 of the filter pockets 230 may be directed toward the borders between the image mounting surface 210 and the extensions 220. Auxiliary entrances 221 may be formed on the borders between the image mounting surface 210 and the extensions 220 and may be cut to correspond to the entrances 231 of the filter pockets 230. When the filter sheets 700 are inserted into the filter pockets 230, the filter sheets 700 may be directly inserted through the shade 200 via the auxiliary entrances 221 without requiring the user to open the cover 400, separate the shade 200, and insert the filter sheets 700 into the separated shade 200.

The filter sheets 700 may further include an illumination part 730 on one side surface thereof.

The illumination parts 730 may be similar to prisms and may be formed of a light transmissive material. Using a property in that light is reflected at a surface, the illumination parts 730 may refract light reflected by the spacer 600 and the extensions 220 toward the image mounting space 210 to additionally illuminate the front side of the image mounting surface 210. Although a light transmissive material with an image directly drawn or printed thereon may be mounted on the image mounting surface 210, a thick image through which light does not transmit almost at all, such as a photo printed on photo paper, may be attached to the image mounting surface 210. In this case, the illumination parts 730 may additionally irradiate light toward the front side of the image, thereby enabling the image to be shown better.

Additionally, in order to apply the illumination parts 730, the spacer 600 and the extensions 220 may be formed of a light transmissive material to easily deliver light to the illumination parts 730. Furthermore, the entrances 231 of the filter pockets 230 may be directed toward the borders between the image mounting surface 210 and the extensions 220, and the auxiliary entrances 221 through which the filter sheets 700 pass may be additionally formed on the borders between the extensions 220 and the image mounting surface 210 to correspond to the entrances 231 of the filter pockets 230. The filter sheets 700 may be introduced into the filter pockets 230 via the auxiliary entrances 221. Therefore, the filter sheets 700 may be mounted without separating the shade 200 or the cover 400. Also, if the illumination parts 730 have a greater width than the auxiliary entrances 221, the illumination parts 730 cannot naturally pass through the auxiliary entrances 221 and by only inserting the filter sheets 700 into the filter pockets 230, the illumination parts 730 may be situated at easy locations (ahead of the borders between the extensions 220 and the image mounting surface 210) to reflect transmitted light. Although the reflected light is basically used to illuminate an image, the reflected light may be concentrated on a desired location on the photochromic layer 710 and the sensitive layer 720, which are applied to the filter sheets 700, thereby raising temperature and thus adjusting transparency (or brightness).

The slopes of the illumination parts 730 may be basically controlled by exerting force on the filter sheets 700, for example, by pressing the filter sheets 700 with a finger, in view of the flexibility of the filter sheets 700. However, the control may fail to maintain the angles of the illumination parts 730 due to the restoring force that will tend to bring the filter sheets 700 to the original form. Accordingly, illumination accommodating parts 740 may be provided on the portions of the filter sheets 700 on which the illumination parts 730 are mounted.

The illumination accommodating parts 740 may be formed of a light transmissive material to facilitate introduction of light into the illumination parts 730. Each of the illumination accommodating parts 740 may include a plurality of light transmissive surfaces 741 having different slopes to form a polyhedron and accommodating recesses 742 that are formed in the centers of the light transmissive surfaces 741, respectively, and into which a portion (preferably, a lower portion) of the corresponding illumination part 730 is fixedly inserted. Accordingly, unlike in conventional control methods, the light reflection region of the illumination part 730 may be more easily controlled by fixedly inserting the illumination part 730 into the accommodating recess 742 at a desired location and then performing additional fine control by bending the filter sheet 700 with a small force. In addition, the filter sheets 700 may each have a plurality of cutting lines (not illustrated) formed on the surface thereof to facilitate bending.

The extensions 220 and the auxiliary flavoring surfaces 640 in the spacer 600 may have at least one air flow hole 751 formed therein, through which air flows. The air flow holes 751 may be formed to face each other and may serve as one air flow channel. However, the air flow holes 751 may be formed so as not to face each other because sufficient air can flow between the extensions 220 and the auxiliary flavoring surfaces 640. The spacer 600 (particularly, the auxiliary flavoring surfaces 640) may be formed of an elastic material (e.g., rubber or a synthetic resin), and the auxiliary flavoring surfaces 640 may rotate left and right according to an air flow through the air flow holes 751. This configuration may use a convection phenomenon that takes place while air is being heated by heat that the lighting column 300 generates in the sealed space. It is widely known that the convection phenomenon induces an air flow sufficient to rotate a pinwheel. Accordingly, air introduced through the air flow holes 751 may rotate the auxiliary flavoring surfaces 640 left and right while colliding with the auxiliary flavoring surfaces 640.

In order to facilitate the rotation of the auxiliary flavoring surfaces 640, each of the auxiliary flavoring surfaces 640 may further include at least one cut-away portion 752 that extends from the surrounding area of the air flow hole 751 in the height direction of the auxiliary flavoring surface 640. The auxiliary flavoring surface 640 may easily rotate left and right with respect to the cut-away portion 752.

As mentioned above, the spacer 600 formed of a transparent material may be used as a passage through which light is reflected to the outside, and therefore the passage may provide a kind of glittering effect while shaking left and right. Accordingly, more dramatic lighting effects can be achieved by adjusting the reflection positions of the illumination parts 730 via the illumination accommodating parts 740 and simultaneously providing a glittering effect induced by the rotation of the auxiliary flavoring surfaces 640.

While the configurations and the corresponding effects of the image-replaceable functional advertisement apparatus according to the inventive concept have been described, it is to be understood that the inventive concept is not limited thereto, but, on the contrary, is intended to cover various modifications and equivalent arrangements included within the spirit and scope of the appended claims.

The inventive concept can be applied to various industrial fields since mass production is possible. Therefore, the inventive concept is industrially applicable.

While the inventive concept has been described with reference to embodiments, it will be apparent to those skilled in the art that various changes and modifications may be made without departing from the spirit and scope of the inventive concept. Therefore, it should be understood that the above embodiments are not limiting, but illustrative.

What is claimed is:

1. An image-replaceable functional advertisement apparatus comprising:
    a base having a plate shape;
    a shade formed of a flexible material and coupled to a top of the base along a periphery of the base, the shade including an image mounting surface to which an image is attached;
    a lighting column mounted in an upright position on a side of an upper surface of the base surrounded by the shade; and
    a cover configured to cover an open top of the shade,
    wherein the shade further includes an opening cut along a height direction of the shade and extensions extending inward from opposite ends of the opening, and
    wherein the base includes a fixing recess into which lower portions of the extensions are fixedly inserted, the fixing recess being concavely formed at a location corresponding to the extensions.

2. The image-replaceable functional advertisement apparatus of claim 1, wherein the lighting column includes a column portion and a support positioned at an end portion of the column portion, the support has a width that is greater than a width of the column portion, the support includes a portion that is protruded along a periphery of the column portion, and the protruded portion of the support is configured to support the cover.

3. The image-replaceable functional advertisement apparatus of claim 2, wherein the cover includes a light coupling portion that has an opening, and
    wherein the lighting column further includes a touch switch positioned on an end portion of the lighting column, the touch switch being exposed to the outside through the opening of the cover and configured to recognize a touch signal and perform on/off control of the LED.

4. The image-replaceable functional advertisement apparatus of claim 1, wherein the base includes a flavoring agent holder including:
    a flavoring agent configured to release a scent;
    a circular holder base seated on a surface of the base; and
    a positioning guide configured to circularly surround a periphery of the holder base to form a flavoring agent storage space in which the flavoring agent is stored.

5. An image-replaceable functional advertisement apparatus comprising:
    a base having a plate shape;
    a shade formed of a flexible material and coupled to a top of the base along a periphery of the base, the shade including an image mounting surface to which an image is attached;
    a lighting column mounted in an upright position on a side of an upper surface of the base surrounded by the shade; and
    a cover configured to cover an open top of the shade,
    wherein the base includes a flavoring agent holder including:
        a flavoring agent configured to release a scent;
        a circular holder base seated on a surface of the base; and
        a positioning guide configured to circularly surround a periphery of the holder base to form a flavoring agent storage space in which the flavoring agent is stored, and
    wherein the cover includes a plurality of flavoring holes formed through the cover.

6. An image-replaceable functional advertisement apparatus comprising:
    a base having a plate shape;
    a shade formed of a flexible material and coupled to a top of the base along a periphery of the base, the shade including an image mounting surface to which an image is attached;
    a lighting column mounted in an upright position on a side of an upper surface of the base surrounded by the shade; and
    a cover configured to cover an open top of the shade,
    wherein the base includes a flavoring agent holder including:
        a flavoring agent configured to release a scent;
        a circular holder base seated on a surface of the base; and
        a positioning guide configured to circularly surround a periphery of the holder base to form a flavoring agent storage space in which the flavoring agent is stored,
    wherein the shade further includes an opening cut along a height direction of the shade and extensions extending inward from opposite ends of the opening,
    wherein the base further includes a fixing recess into which lower portions of the extensions are fixedly inserted, the fixing recess being concavely formed at a location corresponding to the extensions,
    wherein the advertisement apparatus further includes a spacer including:
        auxiliary flavoring surfaces obliquely extending toward the inside of the shade in spaces between the image mounting surface and the extensions and having a greater length than the extensions;
        auxiliary insertion surfaces extending from inside ends of the auxiliary flavoring surfaces in parallel to a virtual extension line that connects distal ends of the pair of extensions;
        auxiliary extension surfaces perpendicularly extending from inside ends of the auxiliary insertions surfaces toward a space between the extensions and having a smaller length than the auxiliary flavoring surfaces; and
        a flavoring extension surface configured to connect outside ends of the auxiliary extension surfaces and including a plurality of flavoring holes formed through the flavoring extension surface at predetermined intervals along the height direction of the shade, and wherein the extensions are inserted into spaces surrounded by the auxiliary flavoring surfaces, the auxiliary insertion surfaces, and the auxiliary extension surfaces, with distal ends of the auxiliary flavoring surfaces spaced apart from each other.

7. The image-replaceable functional advertisement apparatus of claim 6, wherein the spacer further includes:
a plurality of spacing protrusions on outer sides of the auxiliary flavoring surfaces, the plurality of spacing protrusions being formed of an elastic material and protruding at predetermined intervals along a lengthwise direction of the auxiliary flavoring surfaces.

8. The image-replaceable functional advertisement apparatus of claim 7, wherein heights of the spacing protrusions gradually increase along the lengthwise direction of the auxiliary flavoring surfaces.

9. The image-replaceable functional advertisement apparatus of claim 6, wherein the image mounting surface includes:
filter pockets mounted on a back side of the image mounting surface, each of which is formed of a light transmissive material and has an entrance formed at one side and a storage space formed inside; and
filter sheets inserted into the filter pockets and configured to lower illuminance of light transmitting through the filter sheets and provide the light to the image mounting surface.

10. The image-replaceable functional advertisement apparatus of claim 9, wherein the filter sheets include:
a photochromic layer coated with thermochromic pigment, the transparency of which varies according to a temperature change; and
a sensitive layer laminated on the photochromic layer and coated with thermally sensitive pigment that has a temperature change section different from a temperature change section of the photochromic layer.

11. The image-replaceable functional advertisement apparatus of claim 10, wherein the spacer and the extensions are formed of a light transmissive material,
wherein the entrances of the filter pockets are formed in a direction toward borders between the image mounting surface and the extensions,
wherein auxiliary entrances through which the filter sheets are introduced are additionally formed on the borders between the extensions and the image mounting surface, and
wherein the filter sheets further include a three-dimensional illumination part formed of a light transmissive material and configured to refract light reflected by the spacer and the extensions toward the image mounting surface, and the illumination part has a greater width than the auxiliary entrances.

12. The image-replaceable functional advertisement apparatus of claim 11, wherein the filter sheets further include an illumination accommodating part formed of a light transmissive material, the illumination accommodating part including a plurality of light transmissive surfaces having different slopes and accommodating recesses concavely formed in the plurality of light transmissive surfaces, respectively,
wherein the extensions and the auxiliary flavoring surfaces have an air flow hole formed therein, through which air flows,
wherein the auxiliary flavoring surfaces further include a cut-away portion formed of an elastic material and extending from a surrounding area of the air flow hole in a height direction of the auxiliary flavoring surfaces, and
wherein the auxiliary flavoring surfaces rotate left and right with respect to the cut-away portions according to the air flow.

13. The image-replaceable functional advertisement apparatus of claim 6, wherein the flavoring agent contains any one selected from methoxybenzoic acid and sodium benzoate as an effective gradient,
wherein any one of the flavoring holes in the spacer is a sub-hole that has a larger area than the other flavoring holes, and
wherein a flavoring-agent replacement guide apparatus coupled to the sub-hole includes:
a stationary part formed of a transparent material and fixedly inserted into the sub-hole;
a stationary wall extending toward the inside of the shade along a periphery of the stationary part and forming a mounting space with the stationary part;
an opening formed at one side of the stationary wall that is opposite the stationary part; and
an indicator embedded in the mounting space, the indicator being a mixture of any one indicating agent selected from metanil yellow, methyl orange, methyl red, cresolphthalein, thymolphthalein, bromothymol blue, and alizarine yellow R and any one adhesive selected from an acrylic adhesive and a silicone adhesive.

* * * * *